United States Patent [19]

Maryanoff

[11] Patent Number: 4,649,204

[45] Date of Patent: Mar. 10, 1987

[54] DIALKANOLAMINE DERIVATIVES

[75] Inventor: Bruce E. Maryanoff, New Hope, Pa.

[73] Assignee: McNeilab, Inc., Fort Washington, N.J.

[21] Appl. No.: 782,148

[22] Filed: Sep. 30, 1985

Related U.S. Application Data

[63] Continuation of Ser. No. 497,338, May 23, 1983, abandoned, which is a continuation-in-part of Ser. No. 298,962, Sep. 3, 1981, abandoned.

[51] Int. Cl.$^4$ .................. C07C 87/28; C07D 207/00
[52] U.S. Cl. .................. 548/541; 260/501.1; 260/501.18; 514/425; 514/648; 564/316
[58] Field of Search ............... 548/541; 564/320, 316; 260/501.1, 501

[56] References Cited

U.S. PATENT DOCUMENTS

| | | | |
|---|---|---|---|
| 3,157,656 | 11/1964 | Krapcho | 564/320 X |
| 3,342,829 | 9/1967 | Schorr et al. | 564/316 X |
| 3,467,675 | 9/1969 | Petersen et al. | 564/320 X |
| 3,700,680 | 10/1972 | Kaneko et al. | 564/316 X |
| 3,794,645 | 2/1974 | Pieper et al. | 564/320 X |
| 3,855,294 | 12/1974 | Podesva et al. | 564/366 X |
| 3,895,057 | 7/1975 | Kaneko et al. | 564/316 |

FOREIGN PATENT DOCUMENTS 1526188  4/1968  France .......................... 564/316

OTHER PUBLICATIONS

Kloska, "Jour fur Prakische Chemie", vol. 311, pp. 520–522 (1969).

Kjaer et al., "Peta Chemica Scandi", vol. 5, pp. 1145–1150 (1951).

Cattaneo et al., "Farmaco. Sci. Edit. (Italy)", vol. 17, pp. 308–319 (1982).

Primary Examiner—Robert V. Hines
Attorney, Agent, or Firm—David J. Levy

[57] ABSTRACT

Dialkanolamines and nontoxic pharmaceutically-acceptable acid-addition salts of the compounds of the following formula

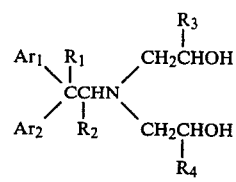

wherein $R_1$ is hydrogen lower alkyl, or fluoro; $R_2$ is hydrogen or lower alkyl; $R_3$ and $R_4$ are the same or different and selected from the group consisting of hydrogen or lower alkyl or $R_3$ and $R_4$ together define a chemical bond directly linking the two alkanol chains so as to form a pyrrolidine ring; Ar, is phenyl or thienyl or phenyl substituted with one to three substituents selected from the group consisting of lower alkyl and halo; and $Ar_2$ is phenyl and phenyl substituted with one to three substituents selected from the group consisting of lower alkyl and halo which have antidepressant activity.

11 Claims, No Drawings

DIALKANOLAMINE DERIVATIVES

The present application is a continuation of U.S. Ser. No. 497,338 filed May 23, 1983 and now abandoned which is a continuation-in-part of my application, Ser. No. 06/298,962 filed Sept. 3, 1981 and now abandoned.

This invention relates to novel chemical compounds, which are derivatives of dialkanolamines, and nontoxic, pharmaceutically acceptable salts thereof.

The dialkanolamines of the present invention are represented by Formula I

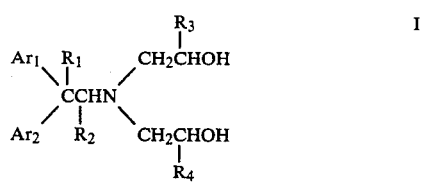

and also the nontoxic, pharmaceutically-acceptable acid-addition salts thereof, wherein $R_1$ is hydrogen, lower alkyl, or fluoro; $R_2$ is hydrogen or lower alkyl; $R_3$ and $R_4$ are the same or different and selected from the group consisting of hydrogen or lower alkyl, or $R_3$ and $R_4$ taken together define a chemical bond directly linking the two alkanol chains so as to form a pyrrolidine ring; $Ar_1$ is phenyl or thienyl or phenyl substituted with one to three substituents selected from the group consisting of lower alkyl and halo; and $Ar_2$ is phenyl or phenyl substituted with one to three substituents selected from the group consisting of lower alkyl and halo. The one to three optional phenyl substituents (per Ar group) which are encompased in Formula I, can be mixed in any manner, and in any substitution pattern.

Typical acid-addition salts are those formed by reacting the base (I) with an equivalent of a pharmacologically acceptable acid (HX) such as, for example, hydrochloric hydrobromic, sulfuric, nitric, phosphoric, fumaric, benzoic, acetic, lactic, hexamic, benzene sulfonic and the like acids.

As used herein, "lower alkyl" means a straight- or branched-chain hydrocarbon containing one to six carbon atoms (such as methyl, ethyl, 2-butyl, and the like. The term halo or halogen is generic to fluorine, chlorine, bromine, and iodine.

The novel compounds of Formula I constitute valuable therapeutic agents by their possession of a pharmaceutically desirable activity. In particular, said compounds are useful in that they possess antidepressant activity.

The new compounds of the present invention can be prepared by various methodologies well-known to those skilled in the art of organic chemistry. Some representative synthetic routes are:

(1) Condensation of a diarylethylamine with an appropriate oxirane compound, e.g.,

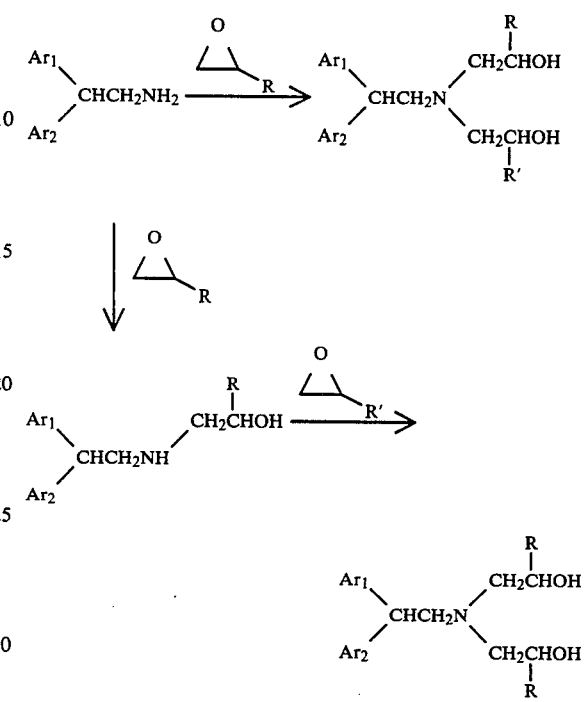

(2) Reaction of a diarylacetaldehyde with a diethanolamine, followed by reduction with a metal hydride such as sodium borohydride, or followed by treatment with a Grignard reagent, e.g.,

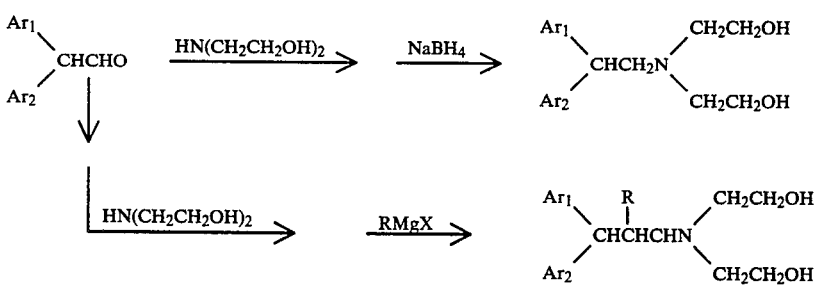

(3) Reaction of a diarylacetic acid derivative with a diethanolamine, followed by reduction with a metal hydride such as lithium aluminum hydride, e.g.,

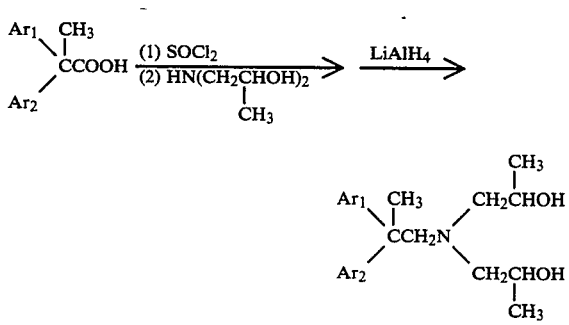

(4) Condensation of a tartaric acid with a diaryle-thylamine, followed by reduction with a metal hydride such as LiAlH$_4$, e.g.,

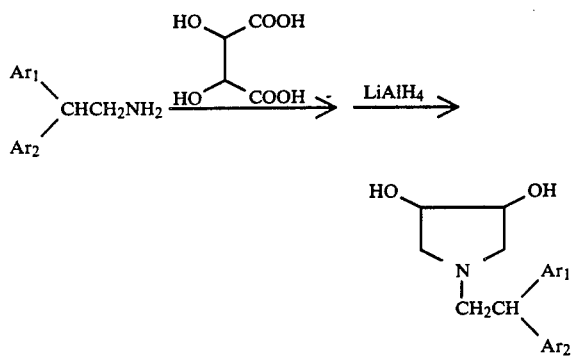

(5) Alkylation of a diarylethylamine with an α-haloa-cetic ester, followed by reduction with a metal hydride such as LiAlH$_4$, e.g.,

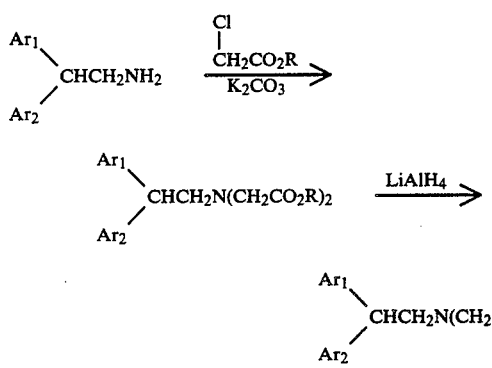

The compounds of this invention can be prepared and utilized in the form of the free base. The compounds can also be used as pharmaceutically-acceptable, nontoxic addition salts of inorganic or organic acids (HX) such as halogen acids, sulfuric acid, maleic acid, hexamic acid, and the like.

The novel compounds of this invention are useful as antidepressant agents.

The antidepressant activity was determined using the "classical" tetrabenazine (TBZ) antagonism test. The antagonism of the decrease in exploratory activity and ptosis, induced by tetrabenazine in mice, has been employed as an experimental model of depression for the study of the antidepressant activity of imipramine and amitriptyline [Vernier, V. G., Hanson, M. H., and Stone, C. A., 1962, in Psychosomtic Medicine, eds. J. H. Nodine and J. H. Moyer (Lea and Febiger, Philadelphia) p. 683].

Various compounds, when studied with respect to their effect on the decrease in exploratory activity and ptosis induced with tetrabenazine in mice, show positive antidepressant activity.

The effect of the compounds on the decrease in exploratory activity and ptosis induced with tetrabenazine in mice is demonstrated by the method of Vernier, V. G., et al. (cited above).

Mice are injected with the test compound 30 minutes prior to the injection of 32 mg/kg i.p. of tetrabenazine. Thirty minutes post tetrabenazine, the mice are tested for the presence of normal exploratory activity and ptosis. A group of 10 mice injected with 32 mg/kg i.p. serve as controls. Three to five dosage levels, 10 mice per dosage level, are used per compound. The dose of the test compound that would be expected to antagonize (i.e., to revert to normal as compared to untreated mice) the aforementioned effects of tetrabenazine in 50% of mice so tested ED$_{50}$ and 95% confidence limits, are calculated according to the probit method of Finney (Finney, D. J., 1964, Probit Analysis, 2nd Edition, University Press, Cambridge, p. 236). When the response to tetrabenazine in the control group is 90% or less, a correction is made for "natural mortality" using Abbott's formula (Finney, D. J., 1964, Probit Analysis, 2nd Edition, University Press, Cambridge, p. 88).

The activities exhibited by the compounds of this invention may be understood by some representative, nonlimiting examples, presented in Table I.

The invention will be further understood by referring to the following examples which illustrate the preparation of compounds according to the invention. These examples are given for the purpose of illustration and are not to be construed as limiting the invention in spirit or scope.

TABLE I

| Compound of Example No. | Compound | HX | TBZ ED$_{50}$ EA/Pt, i.p. |
|---|---|---|---|
| I | (C$_6$H$_5$)$_2$CHCH$_2$N(CH$_2$CH$_2$OH)$_2$ | HCl | 15/1.5 mg/kg |
| II | (C$_6$H$_5$)$_2$C(CH$_3$)CH$_2$N(CH$_2$CH$_2$OH)$_2$ | HCl | 28/35 |
| V | (C$_6$H$_5$)$_2$CHCH(CH$_3$)N(CH$_2$CH$_2$OH)$_2$ | fumarate | 13/8 |
| IV | (C$_6$H$_5$)$_2$CHCH(C$_2$H$_5$N(CH$_2$CH$_2$OH)$_2$ | fumarate | 23/19 |
| III | (C$_6$H$_5$)$_2$CHCH$_2$N[CH$_2$CH(CH$_3$)OH]$_2$ | HCl | 11/6 |
| VI |  | HI | ~60/~60 |
| VII |  | [Base] | ~60/~60 |
| IX | 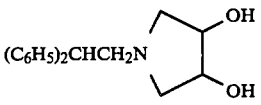 | ½ fumarate | 35/6 |

TABLE I-continued

| Compound of Example No. | Compound | HX | TBZ ED$_{50}$ EA/Pt, i.p. |
|---|---|---|---|
| VII | $(C_6H_5)_2CFCH_2N(CH_2CH_2OH)_2$ | 2 hexamate | 40/12 |

EXAMPLE I 2,2'-[(2,2-Diphenylethyl)imino]bis[ethanol]Hydrochloride 16.0 g (0.08 mole) of 2,2-diphenylethylamine is dissolved in 40 ml of methanol and two drops of conc. HCl are added. The mixture is cooled to 0° and treated with a cold (0°) solution of 18 ml of ethylene oxide in 10 ml of methanol. The reaction is heated at reflux for one hour, cooled, and concentrated in vacuo to a viscous oil. About 200 ml of dry ether is added and the solution is decanted from any minor amounts of solid. It is then treated with anhydrous hydrogen chloride to give a light tan solid, which is collected by filtration. Recrystallization twice from a mixture of ethylacetate/methanol affords a pure white solid product, m.p. 163.5°–165° C.

EXAMPLE II 2,2'-[(2,2-Diphenylpropyl)imino]bis[ethanol]Hydrochloride

This compound is prepared from 2,2-diphenylpropylamine and ethylene oxide according to the procedure of Example I with a three-hour reflux. Recrystallization of the HCl salt twice from ethylacetate/methanol gives a white solid product, m.p. 183°–184.5° C.

EXAMPLE III 1,1'-[(2,2-Diphenylethyl)imino]bis[2-propanol].HCl (VII)

This compound, actually a mixture of two diastereomers because of the chiral centers of the propanol groups, is prepared from 2,2-diphenylethylamine and propylene oxide according to the procedure of Example I. The crude, oily product shows both diastereomers by $^1$HNMR and TLC (ethylacetate/95% ethanol, 5:1, silica gel), in a ratio of ca. 1:1. Recrystallization of the HCl salt from ethylacetate/methanol results in a partial separation of the meso and dl diastereomers. The less soluble, first fraction, is recrystallized again to give a higher melting mixture, enriched in one isomer (ca. 85%), m.p. 171°–179° C. The mother liquor from the first recrystallization is diluted with dry ether to induce material enriched in the other isomer to separate. The more soluble, second fraction is recrystallized again to give a lower melting mixture, enriched in the other isomer (ca. 75%), m.p. 146°–155° C.

EXAMPLE IV 2,2'-[(1,1-Diphenyl-2-butyl)imino]bis[ethanol]Fumarate

A mixture of 60 g (0.306 mole) of diphenylacetaldehyde and 32.4 g (0.308 mole) diethanolamine in 60 ml of toluene is heated at reflux for 1.5 hours, using a Dean-Stark trap to collect the water that is generated. The toluene is distilled in vacuo to leave a viscous oil. 19.9 g of this oil in 100 ml of dry ether is added slowly to 76 ml of 3M ethylmagnesium bromide in ether. After two hours, 200 ml of water is added. The organic layer is separated and rinsed with brine, dried over $Na_2SO_4$, and concentrated to a yellow viscous oil. Part of this oil is chromatographed on silica gel; 3.0 g of the purified material is converted into a salt with fumaric acid. Recrystallization twice from ethylacetate/methanol gives a white solid, m.p. 155°–157.5° C.

EXAMPLE V 2,2'-[(1,1-Diphenyl-2-propyl)imino]bis[ethanol]Fumarate 15.5 g of intermediate brown oil from Example IV is added to 55 ml of 3M methylmagnesium bromide in ether. This preparation is conducted in the same manner as that in Example IV. The crude, oily product was converted to a fumarate salt. Recrystallization twice from ethylacetate/methanol/2-propanol gives a white solid, m.p. 149°–151° C.

EXAMPLE VI 2,2'-{[2-Phenyl]-2-[(2-thienyl)ethyl]imino}bis{ethanol}.HI

This compound is prepared from 2-phenyl-2-(2-thienyl)ethylamine and ethylene oxide according to the procedure of Example VIII. The hydroiodide salt is made and recrystallized twice from ethylacetate/methanol to give a white solid, m.p. 118°–120° C.

EXAMPLE VII 2,2'-{[2,2-Bis(4-chlorophenyl)ethyl]imino}bis{ethanol}

This compound is prepared from 2,2-bis(4-chlorophenyl)ethylamine and ethylene oxide according to the procedure of Example VIII. The crude, free-base product is recrystallized twice from ethylacetate/hexane to give colorless crystals, m.p. 75°–76° C.

EXAMPLE VIII 2,2'-[(2-Fluoro-2,2-diphenylethyl)imino]-bis[ethanol]-Dihexamate 4.3 g of 2,2-diphenyl-2-fluoroethylamine (20 mmole) in 20 ml of methanol (containing one drop of conc. HCl) was cooled to 0° C. and treated with a cold solution of 7 ml of ethylene oxide in 7 ml of methanol. The combined mixture was heated in a sealed pressure flask at 100° C. for 4 hours, cooled, and evaporated to dryness. The residue was chromatographed on 350 g of silica gel using ethylacetate/chloroform saturated with $NH_3$ (10:1) to give a tan oil. The oil was dissolved in 40 ml of dry ether, filtered, and treated with a solution of 1.6 g of hexamic acid in 15 ml of methanol. The white, fluffy solid was recrystallized from ethylacetate/methanol (7:1) to give fine, colorless needles, m.p. 142°–144° C.

EXAMPLE IX 1-(2,2-Diphenylethyl)pyrrolidine-3,4-diol Hemifumarate 9.5 g (0.063 mole) of (+)-tartaric acid in 170 ml of xylenes is heated to reflux and a solution of 15 g (0.075 mole) 2,2-diphenylethylamine in 30 ml of xylenes is added. Water is removed under reflux using a Dean-Stark trap. Reflux is continued for 3 hours. On cooling, a crystalline solid separates. The mixture is cooled further to 0° and is filtered. The crude, tan imide is recrystallized from methanol/water (2:1). 12 g of imide in 100 ml dry tetrahydrofuran (THF) is treated with 75 ml of 1M lithium aluminum hydride in THF over 15 minutes with rapid mechanical stirring. After about 16 hours, some dry ether and water is added. The mixture is filtered and the solids are washed with methylene chloride. The combined filtrates are dried (Na$_2$SO$_4$) and concentrated to an oil, which is converted to a solid fumarate salt. The salt is recrystallized from THF/methanol (10:1) to give light tan solid, a hemifumarate, m.p. 168°–171° C., resolidified, 175°–177° C. (dec), $[\alpha]_D^{24}+6.9°$ (c 0.25, methanol).

The same procedure was applied to (−)-tartaric acid to give the enantiomeric product, m.p. 184°–186° C. (dec), $[\alpha]_D^{23}-8.4°$ (c 0.50, methanol).

For pharmaceutical purposes, the compounds according to the present invention are administered to warm-blooded animals enterally or parenterally as active ingredients in customary dosage unit form consisting essentially of an inert pharmaceutical carrier and one effective dosage unit (1–500 mg) of the active ingredient, such as tablets, coated pills, capsules, wafers, powders, solutions, suspensions, emulsions, syrups, suppositories, and the like.

The following examples illustrate a few pharmaceutical dosage unit compositions comprising a compound of the present invention as an active ingredient and represent suitable modes for putting the invention into practical use. The parts are parts by weight unless otherwise specified.

EXAMPLE XV

Tablets

The tablet composition is compounded from the following ingredients:

| | |
|---|---|
| 2,2'-[2,2-Diphenylethyl)imino]-bis[ethanol] hydrochloride | 100.0 parts |
| Lactose | 45.0 parts |
| Corn Starch | 45.0 parts |
| Colloidal silicic acid | 2.0 parts |
| Soluble starch | 5.0 parts |
| Magnesium stearate | 3.0 parts |
| TOTAL | 200.0 parts |

Preparation

The active ingredient is admixed with part of the excipients, and the mixture is granulated with a solution of the soluble starch in water. After drying of the granulate, the remaining excipients are admixed with it, and the mixture is compressed into 200 mg tablets. Each tablet contains 100 mg of the dialkanolamine compound and is an oral dosage unit with effective antidepressant action.

EXAMPLE XVI

Coated Pills

The pill core composition is compounded from the following ingredients:

| | |
|---|---|
| 2,2'-[(2,2-Diphenylethyl)imino]-bis[ethanol] hydrochloride | 100.0 parts |
| Lactose | 75.0 parts |
| Corn starch | 65.0 parts |
| Colloidal silicic acid | 2.0 parts |
| Soluble starch | 5.0 parts |
| Magnesium stearate | 3.0 parts |
| TOTAL | 250.0 parts |

Preparation

The ingredients are compounded as described in Example V, and the composition is compressed into 250 mg pill cores which are subsequently coated in a conventional manner with a thin shell consisting essentially of a mixture of sugar, talcum and gum arabic. Each coated pill contains 100 mg of the dialkanolamine compound and is an oral dosage unit composition with effective antidepressant action.

EXAMPLE XVII

Syrup

The syrup composition is compounded from the following ingredients:

| | |
|---|---|
| 2,2'-[(2,2-Diphenylethyl)imino]-bis[ethanol] hydrochloride | 100.0 parts |
| Cane sugar | 150.0 parts |
| Glycerol (twice distilled) | 250.0 parts |
| Methyl p-hydroxybenzoate | 3.0 parts |
| Propyl p-hydroxybenzoate | 2.0 parts |
| Flavorings, as desired | |
| Water (distilled) | 1,995.0 parts |
| TOTAL | 2,500.0 parts |

EXAMPLE XVIII

Tablets

The tablet composition is compounded from the following ingredients:

| | |
|---|---|
| 1,1'-[2,2-(Diphenylethyl)imino]bis-2-[propanol] hydrochloride | 100.0 parts |
| Lactose | 20.0 parts |
| Corn Starch | 20.0 parts |
| Colloidal silicic acid | 2.0 parts |
| Soluble Starch | 5.0 parts |
| Magnesium stearate | 3.0 parts |
| TOTAL | 150.0 parts |

Preparation

The active ingredient is admixed with part of the excipients, and the mixture is granulated with a solution of the soluble starch in water. After drying of the granulate, the remaining excipients are admixed with it, and the mixture is compressed into 150 mg tablets. Each tablet contains 100 mg of the dialkanolamine compound and is an oral dosage unit with effective antidepressant action.

EXAMPLE XIX

Coated Pills

The pill core composition is compounded from the following ingredients:

| | |
|---|---|
| 2,2'-[(2-Hydroxy-2,2-diphenylethyl)imino]-bis[ethanol] hydrochloride | 100.0 parts |
| Lactose | 45.0 parts |
| Corn starch | 45.0 parts |

| -continued | |
|---|---|
| Colloidal silicic acid | 2.0 parts |
| Soluble starch | 5.0 parts |
| Magnesium stearate | 3.0 parts |
| TOTAL | 200.0 parts |

Preparation

The ingredients are compounded as described in Example V, and the composition is compressed into 200 mg pill cores which are subsequently coated in a conventional manner with a thin shell consisting essentially of a mixture of sugar, talcum and gum arabic. Each coated pill contains 100 mg of the dialkanolamine compound and is an oral dosage unit composition with effective gastric antisecretory, analgesic and antidepressant action.

I claim:

1. A compound selected from the group consisting of dialkanolamines of the formula:

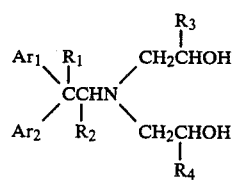

and nontoxic, pharmaceutically acceptable acid addition salts thereof, wherein $R_1$ is hydrogen, lower alkyl, or fluoro; $R_2$ is hydrogen or lower alkyl; $R_3$ and $R_4$ are the same or different and selected from the group consisting of hydrogen or lower alkyl or $R_3$ and $R_4$ taken together define a chemical bond directly linking the two alkanol chains so as to form a pyrrolidine ring; $Ar_1$ is phenyl; and $Ar_2$ is phenyl.

2. A compound of claim 1 which is 2,2'-[(2,2-diphenylpropyl)imino]bis[ethanol] or a nontoxic, pharmaceutically-acceptable acid-addition salt thereof.

3. A compound of claim 1 which is 2,2'-[(2,2-diphenylethyl)imino]bis[ethanol] or a nontoxic, pharmaceutically-acceptable acid-addition salt thereof.

4. A compound of claim 1 which is 2,2'-[(1,1-diphenyl-2-butyl)imino]bis[ethanol] or a nontoxic, pharmaceutically-acceptable acid-addition salt thereof.

5. A compound of claim 1 which is 2,2'-[(1,1-diphenyl-2-propyl)imino]bis[ethanol] or a nontoxic, pharmaceutically-acceptable acid-addition salt thereof.

6. A compound of claim 1 which is 1-(2,2-diphenylethyl)-pyrrolidine-3,4-diol or a nontoxic, pharmaceutically-acceptable acid-addition salt thereof.

7. A compound of claim 1 which is 2,2'-[(2,2-diphenylethyl)imino]bis[ethanol] hydrochloride.

8. A compound of claim 1 which is 2,2'-[(2-fluoro-2,2-diphenylethyl)imino]bis[ethanol] dihexamate.

9. A compound of claim 1, wherein $R_1$ is hydrogen.

10. A compound of claim 1, wherein $R_2$ is hydrogen.

11. A compound of claim 1, wherein $R_3$ and $R_4$ are hydrogen.

* * * * *